United States Patent [19]

Patil et al.

[11] Patent Number: 5,723,631
[45] Date of Patent: Mar. 3, 1998

[54] COUMARIN DERIVATIVES AS RETROVIRAL INHIBITORS

[75] Inventors: Ashok Dharmaji Patil, King of Prussia; Robert Philip Hertzberg, Downingtown; Geoffrey B. Dreyer, Malvern; Alan James Freyer, Downingtown; John W. Westley, Bryn Mawr; Balan Chenera, Audubon, all of Pa.; Michael Leo West, St. Lucia, Australia

[73] Assignee: SmithKline Beecham Corporation, Philadelphia, Pa.

[21] Appl. No.: 464,800

[22] PCT Filed: Dec. 22, 1993

[86] PCT No.: PCT/US93/12500

§ 371 Date: Jun. 22, 1995

§ 102(e) Date: Jun. 22, 1995

[87] PCT Pub. No.: WO94/14789

PCT Pub. Date: Jul. 7, 1994

[51] Int. Cl.$^6$ .................. C07D 311/78; C07D 407/00; C07D 493/12
[52] U.S. Cl. .................. 549/277; 549/289; 549/384
[58] Field of Search .................. 549/277, 384, 549/289

[56] References Cited

U.S. PATENT DOCUMENTS 5,489,697  2/1996  Boulanger et al. .................. 549/278

FOREIGN PATENT DOCUMENTS

WO 93/20082  10/1993  WIPO .
WO 94/28000  12/1994  WIPO .................. 549/277

OTHER PUBLICATIONS

Journal of Medicinal Chemistry, vol. 35, No. 15, Jul. 24, 1992, Kashman et al., "The Calanolides, a Novel HIV–Inhibitory Class of Coumarin Derivatives from the Tropical Rainforest Tree, Calophyllum lanigerum", pp. 2735–2743.

J.C.S. Perkin I, 1977, Gunasekera et al., "Chemical Investigation of Ceylonese Plants, Part 27, Extractives of Calophyllum cuneifolium Thw. and Calophyllum soulattri Burm. f. (Guttiferae)", pp. 1505–1511 1977.

Tetrahedron Letters No. 27, 1972, Gautier et al., "Structure of Calophynic Acid, a Novel Constituent of *Calophyllum inophyllum*", pp. 2715–2718.

Phytochemistry, vol. 25, No. 2, 1986, Bandara et al., "Two Chemically Distinct Groups of Calophyllum Species from Sri Lanka", pp. 425–428.

Bull. Inst. Chem. Res., Kyoto Univ., vol. 50, No. 3, 1972, Kawazu et al., "Piscicidal Constituents of *Calophyllum Inophyllum*", pp. 160–167.

*Primary Examiner*—José C. Dees
*Assistant Examiner*—Barbara Badio
*Attorney, Agent, or Firm*—Alissa M. Eagle; Edward T. Lentz; Stephen A. Venetianer

[57] ABSTRACT

The present invention relates to a process for the preparation of a compound of the following structure:

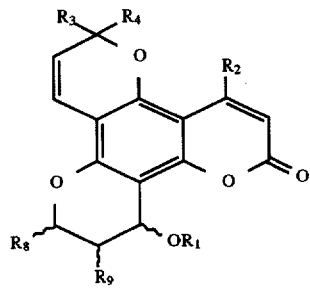

wherein, substituents are as defined in the specification.

8 Claims, No Drawings

COUMARIN DERIVATIVES AS RETROVIRAL INHIBITORS

This application is a 371 of PCT/US 93/12500 filed Dec. 22, 1993.

FIELD OF INVENTION

The present invention relates to compounds which inhibit retroviral infection. The present invention also relates to the synthesis of said compounds and the use of such compounds in clinical applications, such as antiviral therapy. More specifically, this invention relates to certain inophyllum, calanolide and other coumarin derivatives which have antiviral activity.

BACKGROUND OF THE INVENTION

The human immunodeficiency virus (HIV), a retrovirus, is generally accepted as the causative agent of AIDS. Like all retroviruses, a typical retroviral sequence encodes for three genes, gag-pol-env, which actually give rise to multiple proteins by processing reactions. The gag gene gives rise to the protein components of the nucleoprotein core of the virion. The env gene encodes for components of the viral envelope, which also sequesters components from the host cell's cytoplasmic membrane. The pol gene encodes the enzyme reverse transcriptase (RT). Because retroviruses encode their genetic information as RNA, they must undergo reverse transcription of their viral RNA into a DNA copy, which is then integrated into the genome of a host cell. Since mammalian cells do not need RT, this enzyme is an inviting target in a search for anti-viral compounds.

The current AIDS drugs, such as AZT and ddI, are nucleoside analogs which inhibit RT. Although useful, the utility of AZT and related drugs is limited by at least two occurences. The first is that biological resistance often develops to these nucleoside drugs when they are used continuously. The other is that long-term use can be complicated by toxic side effects (Richman et at., *N Engl J Med*, 317:192–197 (1987)). As a result, non-nucleoside inhibitors of RT have been identified, e.g., tetrahydro-imidazo[4,5,1-jk][1,4]-benzodiazepin-2-(1H)-one and -thione (commonly referred to as TIBO), but RT resistance can develop against TIBO compounds as well.

It has been found that some natural products and organisms are potential sources for chemical molecules having biological activity of great diversity, e.g., anti-viral, anti-tumor and anti-fungal properties. The calanolides, a group of natural products from several tropical plants of the genus Calophyllum, are characterized by coumarin, chromane, and chromene ring systems assembled about a phloroglucinol core. Polonsky, J., *Bull. Soc. Chim. Fr.* 914 (1956); Polonsky, J. et al., *Bull. Soc. Chim. Fr*, 929 (1958); Stout, G. H., et al., *J. Org. Chem.* 29; 3604 (1964); Stout, G. H., et al. *J. Org. Chem.* 33:4191 (1968); Gunasekera, S. P., et al. *J. Chem. Soc. Perkin I.* 1505 (1977); Dahrmaratne, H. R. W., et al. *Phytochemistry.* 24:1553 (1984); Kawazu, K., et al. *Bull Inst. Chem. Res. Kyoto Univ,* 50:160 (1972); Calanolide A (20) was recently identified as a potent inhibitor of human immunodeficiency virus-1 reverse transcriptase (HIV-1 RT). Kashman, Y., et al. *J. Med. Chem.* 35:2735 (1992); As with other non-nucleoside HIV-1 RT inhibitors such as TIBO and nevirapine, calanolide-resistant RT mutants have been found. Boyer, P. L., et al. *J. Virology,* 67:2412 (1993); However, the calanolides differ from the other non-nucleosides in the distinct pattern of amino acid changes in RT required to confer resistance, indicating that the RT binding sites for these compounds are overlapping but not identical. (Kohlstaedt, L. A., et al. *Science* 256:1783 (1992)). Further study of calanolide analogues and their RT binding site could therefore aid in identifying drugs or drug combinations less prone to eliciting viral resistance. It is thus an object of the present invention to identify and produce compounds which selectively inhibit retroviral replication presumably due to inhibition of reverse transcriptase.

SUMMARY OF INVENTION

In one aspect, the present invention is a compound represented by the structure:

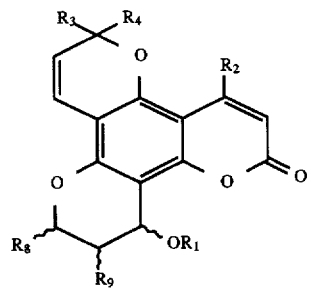

wherein $R_1$ is H, acyl, $COCHR_5NR_6R_7$, $P(O)(OH)_2$ or $S(O)(OH)_2$; wherein:

$R_5$ is H or a side chain of any naturally occurring amino acid; and $R_6$ and $R_7$ are independently selected from the group consisting of H and $C_{1-6}$ alkyl; and $R_6$ and $R_7$ can be taken together to form a 5–7 membered saturated heterocyclic ring containing said nitrogen;

$R_2$ is H, hydroxyl, $C_{1-6}$ alkyl, $C_{1-6}$ alkylamino, di($C_{1-6}$ alkyl)amino, 1-amino-$C_{1-8}$alkyl, $C_{1-8}$ alkyl-amino-$C_{1-8}$ alkyl, di-($C_{1-6}$ alkyl)amino $C_{1-8}$ alkyl, cyclohexyl, aryl or heterocycle, wherein aryl or heterocycle may each be unsubstituted or substituted with one or more of the following: $C_{1-6}$ alkyl, $C_{1-6}$ alkoxy, hydroxy-$C_{1-4}$ alkyl, amino, $C_{1-6}$ alkylamino, di($C_{1-6}$ alkyl)amino, 1-amino-$C_{1-8}$ alkyl, $C_{1-8}$ alkyl-amino-$C_{1-8}$ alkyl, di-($C_{1-6}$ alkyl)amino $C_{1-8}$ alkyl, hydroxyl, nitro, azido or halogen; and $R_3$, $R_4$, $R_8$ and $R_9$ are independently selected from the group consisting of H, methyl and ethyl;

or a pharmaceutically acceptable salt thereof, alone or in combination with a carrier; with the proviso that: when $R_2$ is n-propyl and $R_1$ is H, then $R_8$ and $R_9$ cannot both be methyl; and when $R_2$ is phenyl and $R_1$ is H, then $R_8$ and $R_9$ have a trans relationship to the plane of the molecule and also $R_9$ and $R_1$ have a cis relationship to the plane of the molecule.

In related aspects, this invention comprises compounds represented by the structures:

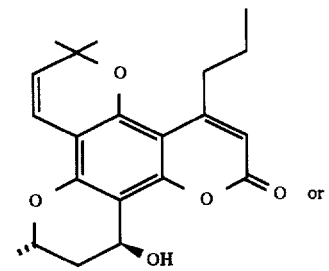

or

3
-continued

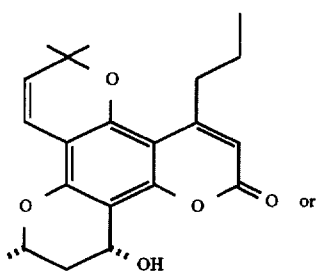

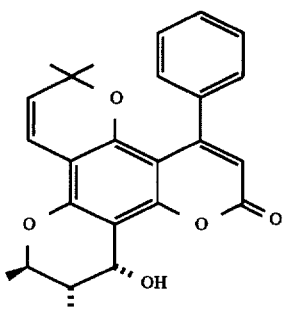

In further related aspects, this invention is two additional compounds represented by the structures:

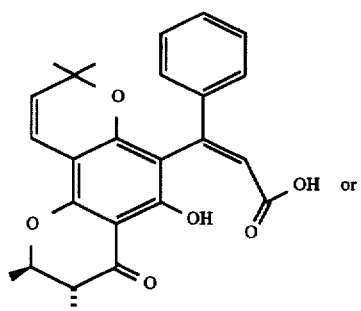

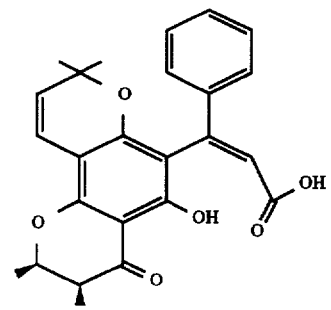

In yet another related aspect, this invention is a pharmaceutical composition comprising an effective, non-toxic amount of the compound(s) of the present invention.

In still another related aspect, this invention relates to a method for treating a mammal infected with a retrovirus which comprises administering to a mammal in need of such treatment an effective, non-toxic amount of the compound(s) of the present invention.

This invention also relates to a process for synthetically preparing the compounds of the instant invention which comprises:(a) reaction of phloroglucinol with a β-ketoacid (or propiolate ester when $R_2$=H) under acid catalysis to form a coumarin lactone ring; (b) acylation with a substituted acryloyl halide and subsequent base-catalyzed ring closure to form a dihydropyran-4-one ring; (c) chromene ring formation by reacting acid and nBu4NI (or KI) with a propargyl halide in the presence of base, and heating to form a chromene pyran ring; and (d) hydride reduction of the tetrahydropyranone keto group.

DETAILED DESCRIPTION

The present invention relates to compounds and use of said compounds for treating viral infections in mammals caused by a broad variety of viruses. In particular, the present invention is useful in treating viral infections caused by retroviruses. More specifically, the present invention relates to compounds which selectively inhibit human immunodeficiency virus (HIV) replication.

The compounds of the present invention relate to a class of coumarin derivatives originally derived from the plant family Guttiferae, genus Calophyllum. The genus Calophyllum is known to comprise at least 175 species of plants (see, e.g., Mabberley, D. J., "The Plant Book", page 92, Cambridge University Press, 1987). The genus has been reported in many tropical locations, from Tahiti to East Africa to Southeast Asia. Among the compounds reported to be isolated from the genus Calophyllum include, triterpenes (Gunatilaka et at., *Phytochem*, 23:323-8 (1984)), xanthones (Kumar, *Phytochem*, 21:807-9 (1982)) and benzopyrans (Stout, *J. Org Chem*, 33:4185-90 (1968)).

In particular, the compounds of the present invention are coumarin derivatives originally dervied from *C. inophyllum* and are represented by the general formula (I):

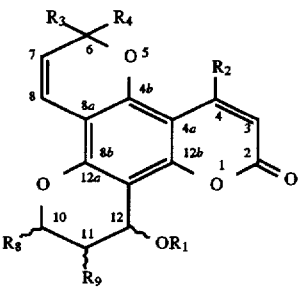

wherein:

$R_1$ is H, acyl, $COCHR_5NR_6R_7$, $P(O)(OH)_2$ or $S(O)(OH)_2$; wherein:

$R_5$ is H or a side chain of any naturally occurring amino acid; and $R_6$ and $R_7$ are independently selected from the group consisting of H and $C_{1-6}$ alkyl; and $R_6$ and $R_7$ can be taken together to form a 5–7 membered saturated heterocyclic ring containing said nitrogen;

$R_2$ is H, hydroxyl, $C_{1-6}$ alkyl, $C_{1-6}$ alkylamino, di($C_{1-6}$ alkyl)amino, 1-amino-$C_{1-8}$ alkyl, $C_{1-8}$ alkyl-amino-$C_{1-8}$ alkyl, di-($C_{1-6}$ alkyl)amino $C_{1-8}$ alkyl, cyclohexyl, aryl or heterocycle, wherein aryl or heterocycle may each be unsubstituted or substituted with one or more of the following: $C_{1-6}$ alkyl, $C_{1-6}$ alkoxy, hydroxy-$C_{1-4}$ alkyl, amino, $C_{1-6}$ alkylamino, di($C_{1-6}$ alkyl)amino, 1-amino-$C_{1-8}$ alkyl, $C_{1-8}$ alkyl-amino-$C_{1-8}$ alkyl, di-($C_{1-6}$alkyl)amino $C_{1-8}$ alkyl, hydroxyl, nitro, azido or halogen; and $R_3$, $R_4$, $R_8$ and $R_9$ are independently selected from the group consisting of H, methyl or ethyl;

or a pharmaceutically acceptable salt thereof, alone or in combination with a carrier; with the proviso that: when $R_2$ is n-propyl and $R_1$ is H, then $R_8$ and $R_9$ cannot both be methyl; and when $R_2$ is phenyl and $R_1$ is H, then $R_8$ and $R_9$ have a trans relationship to the plane of the molecule and also $R_9$ and $R_1$ have a cis relationship to the plane of the molecule.

Preferably $R_1$ is H, $COCHR_5NR_6R_7$, $P(O)(OH)_2$ or $S(O)(OH)_2$. More preferably $R_1$ is H or $COCHR_5NR_6R_7$. Most preferably $R_1$ is H.

Preferably $R_2$ is $C_{1-6}$ alkyl, $C_{1-6}$ alkylamino, di($C_{1-6}$alkyl) amino, cyclohexyl, aryl or heterocycle, wherein aryl or heterocycle may each be unsubstituted or substituted with one or more of the following: $C_{1-6}$ alkyl, $C_{1-6}$ alkoxy, hydroxy-$C_{1-4}$ alkyl, amino, $C_{1-6}$ alkylamino, di($C_{1-6}$ alkyl) amino, 1-amino-$C_{1-8}$ alkyl, $C_{1-8}$ alkyl-amino-$C_{1-8}$ alkyl, di-($C_{1-6}$ alkyl)amino $C_{1-8}$ alkyl, hydroxyl, nitto or halogen. More preferably $R_2$ is $C_{1-3}$ alkyl, $C_{1-6}$ alkylamino, di($C_{1-6}$ alkyl)amino, cyclohexyl, phenyl, a monosubstituted phenyl (with one or more of the following: $C_{1-6}$ alkyl, $C_{1-6}$ alkoxy, hydroxy-$C_{1-4}$ alkyl, amino, $C_{1-6}$ alkylamino, di($C_{1-6}$ alkyl) amino, 1-amino-$C_{1-8}$ alkyl, $C_{1-8}$ alkyl-amino-$C_{1-8}$ alkyl, di-($C_{1-6}$ alkyl)amino $C_{1-8}$ alkyl, hydroxyl, nitro or halogen, but preferably nitro or halogen) or an unsubstituted heterocycle. Still more preferably, $R_2$ is phenyl, p-aminomethylphenyl, methylamino, ethylamino, dimethylamino, methyl, ethyl, n-propyl, isopropyl, cyclohexyl, pyrrolyl, pyrazolyl, imidazolyl, pyridyl, pyrimidinyl, furyl or tetrahydrofuryl. Most preferably, $R_2$ is phenyl, p-aminomethylphenyl, dimethylamino, n-propyl or isopropyl.

Preferably $R_3$ and $R_4$ are both H or methyl.

Preferably $R_8$ and $R_9$ are independently selected from the group consisting of H and methyl.

Preferably, $R_8$ and $R_9$ are in the trans position when $R_2$ is phenyl.

As used herein except where noted: "Alkyl" is intended to include both branched- and straight-chain saturated aliphatic hydrocarbon groups having the specified number of carbon atoms; "aliphatic" is intended to include saturated and unsaturated radicals. This includes saturated or mono or poly unsaturated chains where both double and triple bonds may be present in any combination. "Alkoxy" represents an alkyl group of indicated number of carbon atoms attached through an oxygen bridge. "Acyl" means the radical having a terminal carbonyl carbon. "Halogen" or "halo" as used herein, means fluoro, chloro, bromo or iodo.

"Aryl" would include phenyl, substituted phenyl, biphenyl, substituted biphenyl, naphthyl or substituted naphthyl (wherein substituted comprises one or more of the following: $C_{1-6}$ alkyl, $C_{1-6}$ alkoxy, hydroxy-$C_{1-4}$ alkyl, amino, $C_{1-6}$ alkylamino, di($C_{1-6}$ alkyl)amino, 1-amino-$C_{1-8}$ alkyl, $C_{1-8}$ alkyloamino-$C_{1-8}$ alkyl, di-($C_{1-6}$ alkyl)amino $C_{1-8}$ alkyl, hydroxyl, nitro or halogen).

The term "heterocycle" or "hetercyclic", as used herein except where noted, represents a stable 5- to 7-membered monocyclic or stable 8- to 11-membered bicyclic heterocyclic ring which is either saturated or unsaturated, and which consists of carbon atoms and from one to four heteroatoms selected from the group consisting of N, O, and S, and wherein the nitrogen and sulfur heteroatoms may optionally be oxidized, and the nitrogen heteroatoms may optionally be quaternized, and including any bicyclic group in which any of the above-defined heterocyclic rings is fused to a benzene ring. The heterocyclic ring may be attached at any heteroatom or carbon atom which results in the creation of a stable structure. Examples of such heterocyclic elements include piperidinyl, piperazinyl, 2-oxopiperazinyl, 2-oxopiperidinyl, 2-oxopyrrolidinyl, 2-oxaozepinyl, azepinyl, pyrrolyl, 4-piperidonyl, pyrrolidinyl, pyrazolyl, pyrazolidinyl, imidazolyl, imidazolinyl, imidazolidinyl, pyridyl, pyrazinyl, pyrimidinyl, pyridazinyl, oxazolyl, oxazolidinyl, isoxazolyl, isoxazolidinyl, morpholinyl, thiazolyl, isothiazolyl, quinuclidinyl, isothiazolidinyl, indolyl, quinolinyl, isoquinolinyl, benzimidaz01yl, thiadiazoyl, benzopyranyl, benzothiazolyol, benzoxazolyl, furyl, tetrahydrofuryl, benzofuranyl, tetrahydropyranyl, thienyl, benzothienyl, thiamorpholinyl, thiamorpholinyl, sulfoxide, thiamorpholinyl sulfone, and oxadiazolyl.

When any variable (e.g., aryl, heterocycle, $R^1$, $R^2$, $R^3$, etc.) occurs more than one time in any constituent or in formula I, its definition on each occurrence is independent of its definition at every other occurrence. Also, combinations of substituents and/or variables are permissible only if such combinations result in stable compounds.

The present invention further encompasses derivatives of compounds of the present invention comprising chemical modifications known to those skilled in the art. Chemical modifications include, but are not limited to, hydrolysis, esterification, acetylation, and alkylation, which do not destroy the inhibitory function(s) of the present invention. Furthermore, said modifications retain the ability to inhibit HIV infectivity at substantially the same or lower concentration than the unmodified compounds, but with reduced cytotoxicity.

In addition, when a compound of the present invention contains a chiral center or some other form of an isomeric center, all forms of such isomer(s) are considered to be an aspect of the present invention (e.g., racemic mixtures, enatiomers, etc.).

The compounds of Example 2 can be isolated from the leaves of the tropical rain forest tree *Calophyllum inophyllum*, a large tree commonly found in Southeast Asia. Alternatively, the compounds of the instant invention can be synthesized chemically. For example, a general synthetic scheme to produce compounds of the instant invention may comprise the following steps:

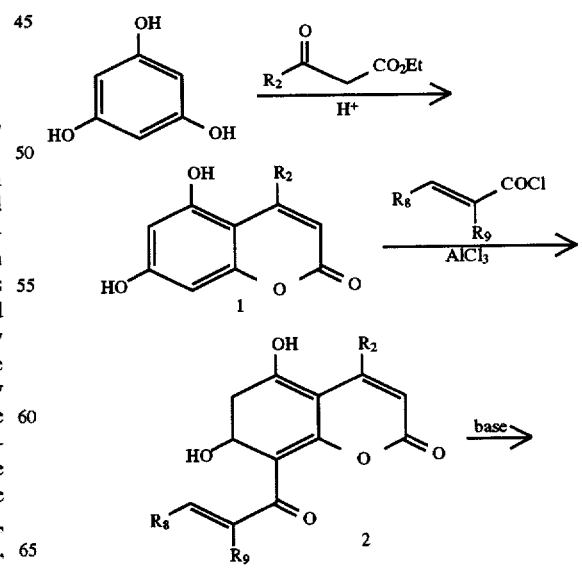

-continued

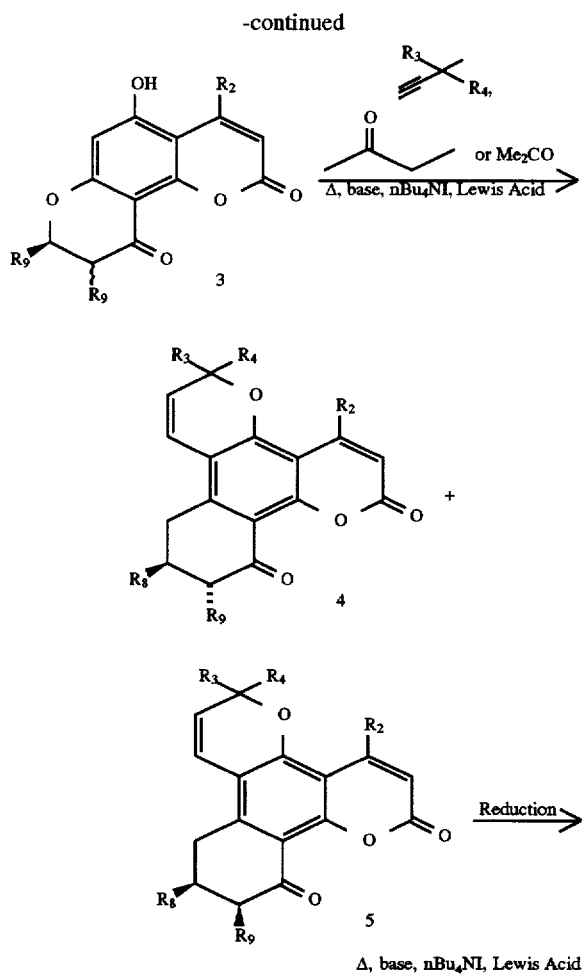

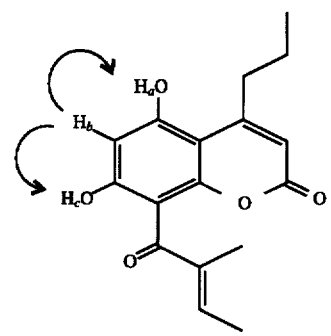

A modified Pechmann reaction (Pechmann et at., *Ber Dtsch Chem Ges*, 16:2127 (1883)) is used to synthesize the coumarin tactones (compound 1) (see, Sethna et al., *Org. Reactions* 7:1 (1953). The modification entails the use of a β-ketoester (or propiolate ester when $R_2$=H) and trifluoromethanesulfonic (triflic) acid as the condensing agent, which results in higher yields and cleaner reactions than reported with other acids. Product yield and purity were improved using neat triflic acid in place of the more usual sulfuric acid catalyst, yielding 1 quantitatively. Good results were also achieved in triflic acid-mediated condensations of phloroglucinol with ethyl acetoacetate or ethyl benzoylacetate. Depending on the nature of $R_2$, one may optionally use protecting groups for this reaction (e.g., CBz, $NO_2$, etc.). Next, a Friedel-Crafts acylation (*Friedel Crafts and Related Reactions*, Vol 3, G. A. Olah (Ed.), Wiley (1963)) with a substituted acryloyl halide results in compound 2. When $R_2$ is n-propyl and $R_8$ and $R_9$ are both methyl, the resulting product, 10 (mp 266°–268 ° C.), was produced in 87% yield. The regiochemistry of acylation in 10 was established by nOe studies showing reciprocal enhancement between the aromatic proton $H_b$ ($\delta_{TMS}$ 6.44 ppm; $CDCl_3$/acetone-$d_6$) and both phenolic hydroxyl protons $H_a$ and $H_c$ ($\delta_{TMS}$ 9.50, 9.87 ppm).

The regiochemical preference of this Friedel-Crafts reaction ensured the desired final arrangement of rings and thus obviated protection strategies. Base treatment (e.g., $K_2CO_3$ refluxing in acetone), (see, e.g., Polonsky et al., *Bull Chim Soc Fr.* 929 (1958) and Stout et al., *J Org Chem*, 29:3604 (1964)) of 10 then led in high yield to a 1:1 epimeric mixture of 2,3-dimethylbenzo-pyranones 3.

C-acylation of 3 with dimethacryloyl chloride followed by ring closure and deoxygenation was not successful in forming the chromene ring. Compound 3 was too deactivated for Friedel-Crafts reaction, and sodium borohydride reduction of 3 led to complex mixtures. Following esterification of 3 with dimethacrylic acid, ketone reduction proceeded readily using $NaBH_4$, but attempted Fries rearrangement of the protected alcohol resulted in decomposition.

Reaction of 3 with a propargyl halide under base catalyst (e.g., $K_2CO_3$) (Hlubucek et al., *Aust J Chem*, 24:2347 (1971)) followed by heating results in a Claisen rearrangement to produce 4 and 5. Aryl propargyl ethers typically undergo rearrangement at 160°–215 ° C. to form ortho-allenyl phenol intermediates, which cyclize to chromenes. In the case of 3, standard conditions for dimethylpropargyl ether formation (3-chloro-3-methylbutyne, $K_2CO_3$, KI or (n-Bu)$_4$NI, 10% DMF in $Me_2CO$ or 2-butanone, 50°–70 ° C.) led to no reaction. However, addition of anhydrous zinc chloride to the reaction mixture resulted in clean formation of chromenes 4 and 5. For example, when 10 was subjected to a base-catalyzed ring closure and subsequent rearrangement, the compounds were formed ($R_8$ and $R_9$ in the trans position, mp 130°–132° C.) and ($R_8$ and $R_9$ in the cis position, mp 130°–131° C.) in a 1.3:1 ratio, respectively, and 61% combined yield after chromatographic separation. The reaction occurs at 40° C. to 160° C., preferably 50° C. to 120° C., and more preferably at 70° C. Without (n-Bu)$_4$NI the reaction proceeded less cleanly and in lower yield, and omitting base (e.g. $K_2CO_3$) resulted in gradual decomposition with no apparent product formation. The presumed propargyl ether intermediate was not detected, but the mild reaction conditions (i.e., 70° C.) suggest that both propargyl ether formation and rearrangement are catalyzed by zinc chloride. Rearrangements of allyl aryl ethers are strongly catalyzed by a variety of Lewis acids including $ZnCl_2$, $BCl_3$, $Et_2AlCl$ and $TiCl_4$ (see, e.g., Karrer et al., *Helv, Chim. Acta.* 21; 520 (1938); Smith et al., *Science*, 88:37 (1938); Fahrni et al., *Helv. Chim, Acta*, 43; 448(1960); Sonnenberg, F. M. *J. Org. Chem.* 35: 3166(1970); Wherli et al., *J. Org. Chem.*, 36:2910 (1971); Borgulya et al., *Helv. Chim. Acta*, 56:14 (1973); Schmidet al., *Helv. Chim, Acta*, 56:105 (1973); Narasakaet al., *Chem. Lett.*, 1041 (1975); and Tachibana, Y. *Bull. Chem. Soc, Japan.* 50: 2477 (1977)) as well as protic acids (see, e.g., Karreret al., *Helv, Chim. Acta.* 21; 1234 (1938); Widmer et al., *Helv. Chim. Acta*, 56: 2644 (1973); Svanholmet al., *Chem. Soc. Perkin II*, 169 (1974); and Ismailet al., *Tetrahedren Lett.*, 3795 (1992)). In addition, rearrangement of aryl propargyl ethers to chromenes has been shown to be catalyzed by mercury and silver salts (see, e.g., Koch-Pomeranzet al., *Helv. Chim. Acta*, 56:2981 (1973)) and by $AlCl_3$ (see, e.g., Bateset et al., *J. Org. Chem.*, 43; 3856 (1978)).

The etherification and rearrangement reaction can be conducted sequentially in the same preparative step. As a last step, the dihydro pyranone keto group of 4 or 5 is reduced to a hydroxyl group yielding compounds of the instant invention. Such compounds may be isolated via chromatographic separation, as described in Example 1. It is also understood that the order of synthesis to produce compounds 4 and 5 under this general synthetic scheme can be varied to yield the same compounds of the invention. In addition, one skilled in the art can synthesize coumarin derivatives lacking methyl groups at ting positions 10 and 11 by selecting the appropriate acryloyl halide.

Furthermore, the compounds of the present invention can be obtained from natural sources by phase extraction chromatography into an organic solvent and then subsequently purified. Such solvents are known to one skilled in the art. For example, the compounds of the invention can be extracted into methyl alcohol, ethyl alcohol, dimethylformamide, dimethyl sulfoxide, ethyl acetate, acetone and the like. Preferred solvents are methyl alcohol or ethyl acetate. However, it is not to be construed that the extraction is limited to just one solvent. More preferably, it is a two-solvent extraction, using two miscible solvents, e.g., methyl alcohol and 1,2-dichloroethane to extract the compounds of the present invention.

The chromatographic separation is carried out by employing conventional chromatography (e.g., gravity, flash, high pressure (i.e., HPLC) or thin layer chromatography (TLC)). Common materials used are alumina and silica gel as well other materials known to one skilled in the art. For example, column chromatography with non-ionic resin or by high performance liquid chromatography employing a reverse phase resin may be used. The fractions containing antiviral activity can be assayed by an in vitro RT assay (e.g., HIV RT) as described more fully below. Generally, more than one chromatographic separation step is employed. In a preferred procedure, one or more separations are carried out employing column chromatography and a final separation is carried out employing preparative thin layer chromatography.

When conventional column chromatography is employed, silica gel is the preferred adsorbent. When more than one chromatographic separation is required, silica gel may be used in all the separations, employing different eluting agents. Such different eluting agent(s) includes the use of two micible solvents in differing ratios. In addition, chromatography using silica gel may be combined advantageously with a different adsorbent, e.g., Sephadex LH-20. Other adsorbents such as alumina, styrene-divinylbenzene copolymers (e.g., HP-20, HP-30, HP-40) and Amberlite (e.g., XAD-2, XAD-4, XAD-16) may also be employed.

A mixture of ethyl acetate and hexanes has been found to be especially useful in the fractionation and recovery of the active compounds of the present invention on silica gel ($SiO_2$). The mixture may be employed in isocratic, step gradient or continuous gradient systems. Once isolated, the fractions containing the homogeneous compound(s) may be concentrated under reduced pressure.

Once synthesized and/or isolated, the purified products can then be analyzed for purity, structure, etc. by such techniques as NMR (e.g., $^1H$, $^{13}C$, DEPT, $^1H$-$^1H$ 2D COSY), MS (fast atom bombardment mass spectrometry (FAB-MS) and Tandem), IR, UV, X-ray and chemical degradation.

Salts of any sort may be made from these compounds, provided that an acidic group or a sufficiently basic nitrogen is present in the compound. Particularly preferred are the pharmaceutically acceptable salts of the instant invention. These salts are defined as those which are acceptable in their application to a pharmaceutical use, meaning that the salt will retain the biological activity of the parent compound and that the salt will not have untoward or deleterious effects in its application and use in treating diseases.

Acid addition salts of the compounds of the present invention are prepared in a standard manner in suitable solvents. In brief, an excess of an acid, such as hydrochloric, hydrobromic, sulfuric, phosphoric, acetic, maleic, or succinic is added to the parent compound. In particular, the acetate salt form is especially useful. In addition, certain of the compounds may form inner salts or zwitterions which may be acceptable. Cationic salts are prepared by treating the parent compound with an excess of an alkylating reagent, such as hydroxide, carbonate or alkoxide containing the appropriate cation. Cations such as $Na^+$, $K^+$, $Ca^{2+}$ and $NH_4^+$ are examples of cations present in pharmaceutically acceptable salts.

The compounds of the instant invention are useful to inhibit the growth or replication of a virus in a mammal. Examples of mammals include humans, primates, bovines, ovines, porcines, felines, canines, etc. Examples of viruses may include but are not limited to HIV-1, HIV-2, herpes simplex virus (types 1 and 2), varicella zoster virus, cytomegalovirus, papilloma virus, HTLV-1, HTLV-2, feline leukemia virus, avian sarcoma viruses such as rous sarcoma virus, hepatitis types A–E, influenza virus, measles, mumps and rubella viruses. More preferably the compounds of the present invention will be used to treat a human infected with a retrovirus. Preferably the compounds of the present invention ,will be used to treat a human exposed or infected (i.e., in need of such treatment) with the human immunodeficiency virus, either prophylactically or therapeutically.

An advantage of certain compounds of the present invention is that they retain the ability to inhibit certain HIV RT mutants which are resistant to TIBO. This is advantageous over the current AIDS drug therapy, where biological resistance often develops to nucleoside analogs used in the inhibition of RT.

Hence the compounds of the present invention are particularly useful in the prevention or treatment of infection by the human immunodeficiency virus and also in the treatment of consequent pathological conditions associated with AIDS. Treating AIDS is defined as including, but not limited to, treating a wide range of states of HIV infection: AIDS, ARC (Aids related complex), both symptomatic and asymptomatic, and actual or potential exposure to HIV. For example, the compounds of this invention are useful in treating infection by HIV after suspected exposure to HIV by e.g., blood transfusion, exposure to patient blood during surgery or an accidental needle stick.

The compounds of the present invention may be assayed for antiviral activity via published protocols. They include, but are not limited to, cell count, cytopathic effect, dish-colony formation, microtiter-growth inhibition and thymidine incorporation. In addition, the compounds of the present invention can be assayed for their ability to inhibit HIV infection via an Infectivity assay. The Infectivity assay comprises infection of T-lymphocytes or macrocyte/macrophages with either HIV- 1 or HIV-2. At six or more days post-infection measurement of particle-associated reverse transcfiptase activity and/or p24 antigen levels can be determined (see, for example, Clapham et al., *Nature*, 337:368–370 (1990) or McDougal et al., *J Immun Meth.* 76:171–183 (1985)). In addition, the focal infectivity assay (FIA) can be used to assay the susceptibility of HIV to antiviral agents (see, e.g., Pincus et al., *BioTechniques.* 10:336–342 (1991)).

Furthermore, the levels of antiviral "activity" of the compounds of the present invention can be rapidly determined in a series of interrelated assays via a semiautomated multiparameter approach as disclosed by Gulakowski et al. (*J Virol Meth,* 33:87–100 (1991)), and is incorporated by reference herein.

Pharmaceutical compositions of the compounds of the present invention may be formulated as solutions of lyophilized powders for parenteral administration. Powders may be reconstituted by addition of a suitable diluent or other pharmaceutically acceptable carrier prior to use. The liquid formulation is generally a buffered, isotonic, aqueous solution. Examples of suitable diluents are normal isotonic saline solution, standard 5% dextrose in water or buffered sodium or ammonium acetate solution. Such formulation is especially suitable for parenteral administration, but may also be used for oral administration. It may be desirable to add excipients such as polyvinylpyrrolidone, gelatin, hydroxy cellulose, acacia, polyethylene glycol, mannitol, sodium chloride or sodium titrate.

Alternatively, the compounds of the present invention may be encapsulated, tableted or prepared in an emulsion or syrup for oral administration. Pharmaceutically acceptable solid or liquid carriers may be added to enhance or stabilize the composition, or to facilitate preparation of the composition. Solid carriers include starch, lactose, calcium sulfate dihydrate, terra alba, magnesium stearate or stearic acid, talc, pectin, acacia, agar or gelatin. Liquid carriers include syrup, peanut oil, olive oil, saline and water. The carrier may also include a sustained release material such as glyceryl monostearate or glyceryl distearate, alone or with a wax. The amount of solid carrier varies but, preferably, will be between about 20 mg to about 1 g per dosage unit. The pharmaceutical preparations are made following the conventional techniques of pharmacy involving milling, mixing, granulating, and compressing, when necessary for tablet forms; or milling mixing and filling for hard gelatin capsule forms. When a liquid carrier is used, the preparation will be in the form of a syrup, elixir, emulsion or an aqueous or non-aqueous suspension. Such a liquid formulation may be administered directly or filled into a soft gelatin capsule.

Carriers or diluents suitable for use are generally known in the pharmaceutical formulary arts. For example, reference to such materials can be found in such well known compilations as *Remington's Pharmaceutical Sciences,* Mack Publishing Co., Easton, Pa., USA.

The dosage ranges for administration of the compounds of the present invention are those to produce the desired affect whereby symptoms of infection are ameliorated. For example, as used herein, a pharmaceutically effective amount for HIV infection refers to the amount administered so as to maintain an amount which suppresses or inhibits secondary infection by syncytia formation or by circulating virus throughout the period during which HIV infection is evidenced such as by presence of anti-HIV antibodies, presence of culturable virus and presence of p24 antigen in patient sera. The presence of anti-HIV antibodies can be determined through use of standard ELISA or western assays for example, anti-gp120, anti-gp41, anti-tat, anti-p55, anti-p17, antibodies, etc. The dosage will generally vary with age, extent of the infection, and counterindications, if any, for example, immune tolerance. The dosage can vary from 0.001 mg/kg/day to 50 mg/kg/day, but preferably 0.01 to 1.0 mg/kg/day.

The pharmaceutical composition may contain other pharmaceuticals in conjunction with the compounds of the instant invention, to treat (therapeutically or prophylactically) acquired immunodeficiency syndrome (AIDS). For example, other pharmaceuticals may include, but are not limited to, other antiviral compounds (e.g., AZT, ddC, TIBO derivatives, acyclovir, α-interferon), immunostimulants (e.g., various interleukins and cytokines), immunomodulators and antibiotics (e.g., antibacterial, antifungal, anti-pneumocysitis agents).

In addition, the compounds of the present invention are useful as tools and/or reagents to study inhibition of retroviral reverse transcriptases. For example, the instant compounds selectively inhibit HIV reverse transcriptase. Hence, the instant compounds are useful as an SAR (structure activity relationships) tool to study, select and/or design other molecules to inhibit HIV.

All publications referenced herein are hereby incorporated by reference in their entireties.

It is believed that one skilled in the an can, using the preceding description, utilize the present invention to its fullest extent. The Examples which follow are illustrative, and not to be construed as limiting of the present invention.

EXAMPLES

General

Proton and $^{13}$C NMR spectra were obtained in the indicated solvent at 400 MHz and 100 MHz, respectively, on a Bruker AMX 400 spectrometer. Chemical shifts (δ) are relative to $(Me)_4Si$, and peak multiplicities are indicated as: s, singlet; d, doublet; t, triplet; q, quartet; m, multiplet; br, broad; dd, doublet of doublets; etc. Desorptive chemical ionization (DCI) mass spectra (MS) were obtained with a Finnigan-MAT quadrupole mass spectrometer. Flash chromatography was performed with E. Merck Kieselgel 60. Preparative HPLC was performed with Dynamax silica (5μ) (Rainin).

1. Collection, Extraction, and Isolation

Leaves and twigs (0.5 kg) of *C. inophyllum* from Malaysia and Ghana were obtained. Extraction with $MeOH:CH_2Cl_2$ by cold percolation procedure yielded a dark green residue (46 g) which displayed strong reverse transcriptase inhibition activity. This residue was triturated with $CH_2Cl_2$ to give a dark green oil (19.5 g). Silica gel (800 g) column chromatography of the $CH_2Cl_2$ soluble portion using EtOAc and hexane mixture starting with EtOAc: hexane mixture (30:70) and then increasing percentages of EtOAc in hexane. Total 550 fractions (15 ml each) were collected and monitored by $SiO_2$ gel tlc. Like fractions were combined to give 20 individual fractions. Fractions 95–107 (1.05 g) after RP-18 column chromatography using $CH_3CN$ as a solvent for elution yielded several fractions. Fractions 22–48 (108 mg) from this column after $SiO_2$ gel hplc (EtOAc: hexane, 25:75) furnished calophyllolide (0.094 g).

The combined residue of fractions 108–134 (0.925 g) from the $SiO_2$ gel column was chromatographed on a column of RP- 18 $SiO_2$ gel ($H_2O$: $CH_3CN$, 5:95) to give several subfractions which after $SiO_2$ gel hplc (EtOAc: hexane, 25:75) gave inophyllum A (0.405 g) and calophyllolide (0.022 g). Fractions 135–180 (0.912 g) after RP-18 column ($CH_3CN$) and $SiO_2$ gel ptlc gave additional inophyllum A (0.437 g) as a major component. A minor sub-fraction (0.018 g) from the RP-18 column which was crystalline and appeared homogeneous by tlc, was resolved using SiO₂ gel hplc (EtOAc:hexane, 25:75) to yield inophyllum P (0.008 g) and inophyllum B (0.0072 g). Another minor sub-fraction (0.022 g) which also appeared to be a single compound by tlc was separated by normal phase hplc (EtOAc:Hex, 25:75) into two compounds of almost same retention times and were identified as novel stereoisomers called G-1, (0.009 g) and G-2, (0.008 g). Fractions 191–235 (0.399 g) from the SiO₂ gel column after repeated ptlc using (Si gel, MeOH:CH₂Cl₂, 3:97 and EtOAc:hexane, 35:65) yielded two compounds which were identified as inophyllums C (0.099 g) and D (0.032 g). Fractions 236–310 (0.638 g) were puttied by SiO₂ gel ptlc (EtOAc:hexane, 35:65) to afford inophyllum E (0.277 g) and also additional amount (0.073 g) of inophyllum C. Residue from fractions 404–466 (0.431 g) was comparatively more polar. Purification using SiO₂ gel ptlc (EtOAc:hexane, 1:1) and finally crystallization from hot EtOAc afforded two acids (Calophyllic acid 0.098 g and Iso-calophyllic acid 0.116 g) whose structure and absolute configuration was determined by X-ray crystallography. Both calophyllic acid and iso-calphyllic acid can be used as intermediates to synthesize certain inophyllums of the present invention (e.g., inophyllums B and P).

2. Structure Determination

The structures of calophylloide and inophyllums A–E were identified and are shown below. The relative stereochemistry of inophyllum B and inophyllum P is of interest because of their sub-micromolar activity in the RT-ase assay. Inophyllum P is a novel inophyllum with a molecular weight of 404; molecular formula, $C_{25}H_{24}O_5$; and uv spectrum of λ max 235, 280, 286 and 337 nm. The ir spectrum of inophyllum P showed bands ascribed to hydroxyl (3435 cm⁻¹), α, β-unsaturated lactone (1719 cm⁻¹) and monosubstituted benzene (765 and 703 cm⁻¹). Inophyllum P was easily acetylated with acetic anhydride and pyridine to give monoacetate, whose 1H nmr spectrum showed a singlet (3H) at δ2.14 ppm suggesting that it is a dihydro derivative in which the C-12 ketone of inophyllum C is replaced by a secondary alcohol group. Comparison of the ¹H nmr spectra of inophyllums A, B, D and P with those of C and E demonstrates that D as well as A are hydroxy analogs of inophyllum E, while B and P are the hydroxy analogs of inophyllum C.

The absolute configuration of inophyllum A was established by X-ray analysis of the 4-bromobenzoate, which was prepared by treatment of inophyllum A with 4-bromobenzoyl chloride in presence of N,N-dimethylamino pyridine. Once an absolute configuration of inophyllum A was established, the relative stereochemistry of the chromen ring in all other inophyllums was readily defined by measuring nOes and coupling constants. A systematic study of the coupling constants and the nOes observed with these compounds leads to general stereochemistry assignments. The coupling constants and hoe (presented as percentage of the maximum possible nOe) are presented at the end of Example 4. For clarity, only the chromen ring is depicted, and the numbering of protons H-10, H-11 and H-12 has been changed to H-1, H-2 and H-3, respectively. The proton assignments of inophyllums A–E agree well with literature values (Gunasekera et al, *J Chem Soc Perkins*, 1:1505–1511 (1977) and Kawazu et al, *Bull Inst Chem Res*, 50:160–167 (1972)). Inophyllum P which has vimally the identical chemical shifts as soulattrolide (Gunasekera et at, supra) has an optical rotation opposite in sign to that published for soulattrolide. Inophyllum P is thus an enantiomer of soulattrolide and epimer of inophyllum B.

This was confirmed by the reduction of Inophyllum C. Treatment of inophyllum C with an excess amount of NaBH₄ in MeOH at room temperature and subsequent work up yielded inophyllum B and inophyllum P. All three compounds, ketone and alcohols share relatively large coupling constants between protons H-1 and H-2 (between 9 and 11 Hz) and relatively small percentages of nOe between protons H-1 and H-2 (between 2 and 7 %). Additionally, the alpha alcohols like inophyllum D, and inophyllum P exhibit small coupling constants between protons H-2 and H-3 (between 2 and 4 Hz), while the beta alcohols like inophyllums A and B gave larger coupling constants between protons H-2 and H-3 (between 5 and 8 Hz). Reduction of inophyllum E gives both Inophyllum A and Inophyllum D. All three share relatively small coupling constants between protons H-1 and H-2 (between 2 and 4 Hz) and relatively large percentages of nOe between protons H-1 and H-2 (between 10 and 21%). The structures of the isolated compounds are presented below.

Calophyllolide

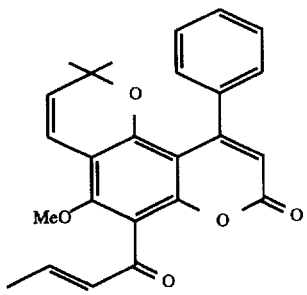

Inophyllum A

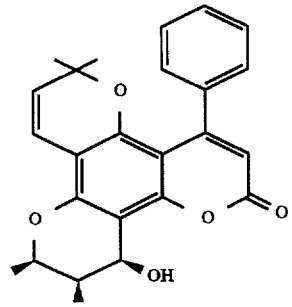

Inophyllum B

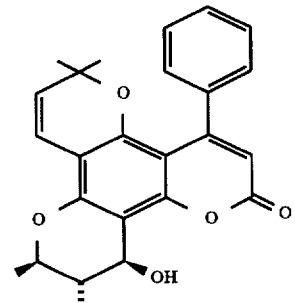

-continued
Inophyllum C
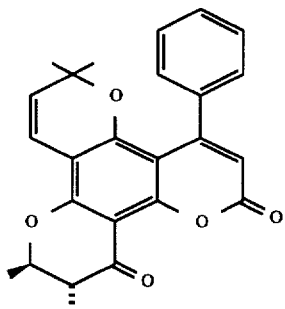
Inophyllum D
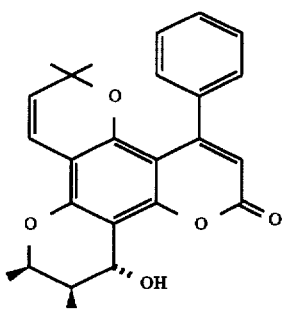
Inophyllum E
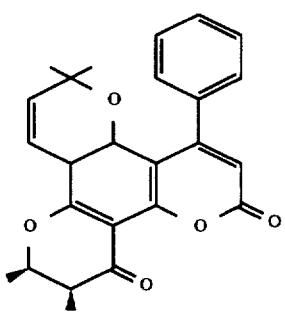
Inophyllum P
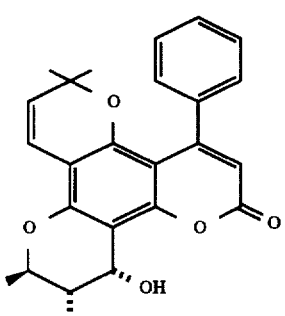
G-1
-continued
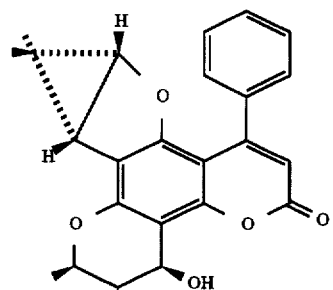
G-2
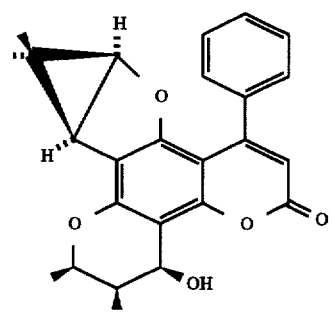
Calophyllic Acid
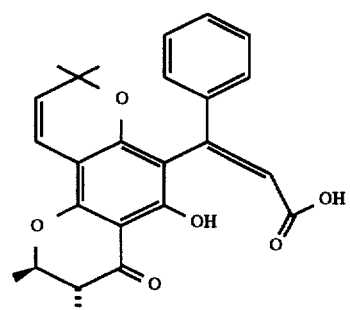
Iso-calophyllic acid
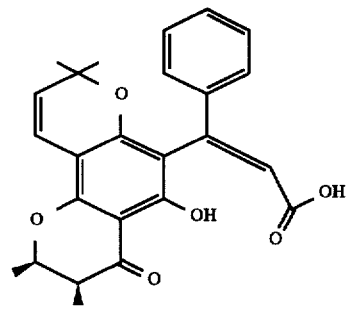

3. Modifications/Derivatives

Reduction of inophyllum C:

Inophyllum C (0.050 g) in methanol (10 ml) was treated with sodium borohydride ( 0.050 g). The mixture was stirred for 12 h at room temperature, the excess of hydride was destroyed with water and product extracted with methylene chloride. The gum obtained on evaporation was separated by silica gel ptlc first with ethyl acetate:hexane (35:65) and second with acetone:hexane (30:70) mixture into two compounds. The more polar compound (0.011 g) was identified as inophyllum P and less polar (0.017.2 g) as inophyllum B.

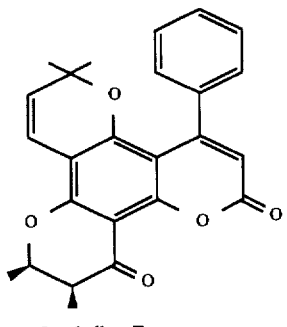

Inophyllum E sodium borohydride in methanol
Stir overnight, dilute with water, extract with methylene chloride, purify residue by Si gel ptlc

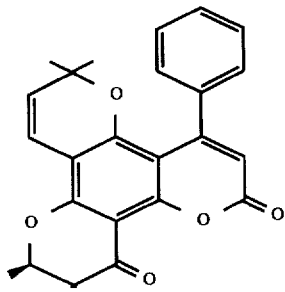

Inophyllum C

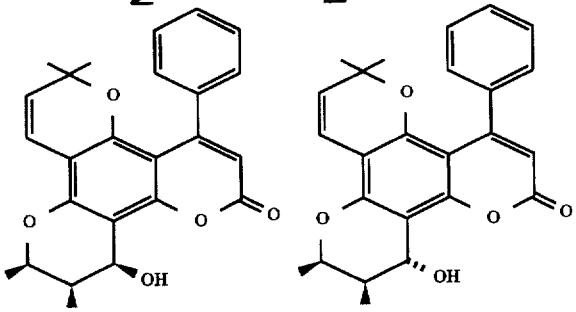

Inophyllum A      Inophyllum D

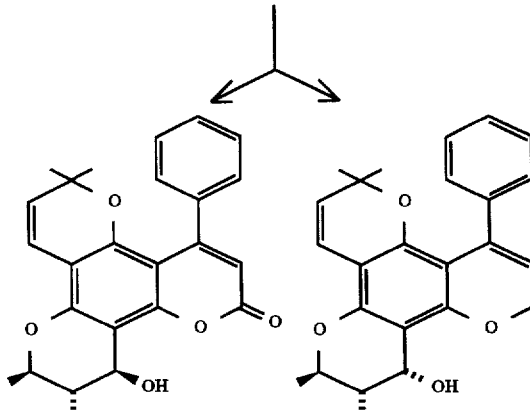

Inophyllum B      Inophyllum P

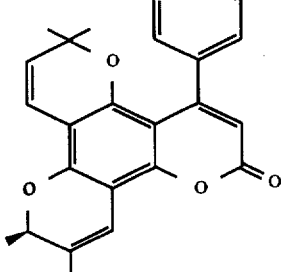

11-anhydro-inophyllum D

Reduction of inophyllum E:

Inophyllum E (0.100 g) in methanol (20 ml) was treated with sodium borohydride (0.100 g). The mixture was stirrod for 12 h. at room temperature, the excess hydride was destroyed with water and product extracted with methylene chloride. The residue obtained after the removal of solvent was purified by silica gel ptlc using ethyl acetate:hexane (40:60) first, and then acetone:hexane (30:70). The less polar compound (0.37 g) which easily crystallized from ethyl acetate was identified as inophyllum A, while more polar compound (0.011 g) as inophyllum D, which later dehydrated to give anhydro inophyllum D.

Preparation of 4-bromobenzoate derivative of inophyllum A:

Inophyllum A (50 mg) was dissolved in acetonitrile (10ml) and to the solution were added N,N-dimethyl amino pyridine (5 mg) and excess amount of 4-bromobenzoyl chloride (100 mg) and stirred at room temperature for 12 h. The reaction mixture was diluted with 0.1N HCl (25 ml) to remove excess 4-bromobenzoyl chloride and extracted with ether (3×25 ml), washed first with $NaHCO_3$ and then with brine and water. Evaporation of ether layer yielded colorless residue. Purification by Si gel ptlc (EtOAc:hexane:30:70) provided pure bromobenzoate Inophyllum A (52 mg) which crystallized from EtOAc as long needles.

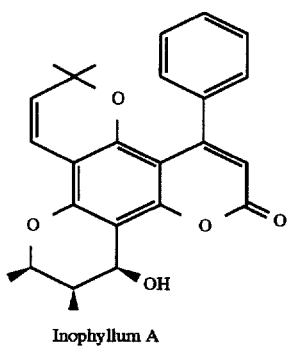

Inophyllum A

Dissolve in acetonitrile and add N—N-dimethyl aminopyridine and 4-bromobenzoyl chloride Stir for 12 h. Dilute with .1N HCl, extract with ether Purify the residue by Si gel ptlc

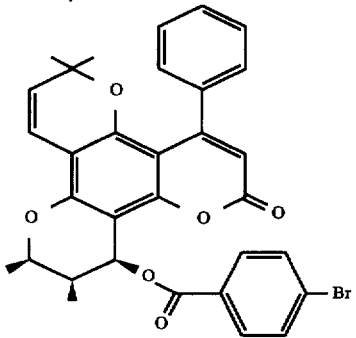

4. Spectral Data

The numbering system for Inophyllum compounds is presented below:

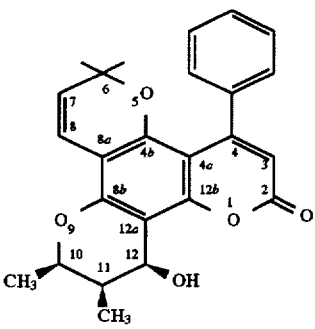

¹H NMR INFORMATION:

| Assignment H# | Inophyllum A Literature | Inophyllum A Observed |
|---|---|---|
| Ph-4 | 7.3 | 7.3 (m) |
| H-8 | 6.55 (d,10) | 6.54 (d,10.0) |
| H-3 | 5.96 (s) | 5.96 (s) |
| H-7 | 5.36 (d,10) | 5.37 (d,10.0) |
| H-12 | 5.17 (d,5.4) | 5.16 (d,5.1) |
| H-10 | 4.43 (m,7.0,3.3) | 4.41 (dq,6.7,3.3) |
| H-11 | 2.27 (m,7.2,3.3,5.4) | 2.31 (ddq,7.1,3.3,5.1) |
| Me-10 | 1.43 (d,7.0) | 1.43 (d,6.7) |
| Me-11 | 1.17 (d,7.2) | 1.17 (d,7.1) |
| Me-6 | 0.94 (s) | 0.95 (s), 0.93 (s) |

| Assignment H# | Inophyllum B Literature | Inophyllum B Observed |
|---|---|---|
| Ph-4 | 7.3 | 7.3 (m) |
| H-8 | 6.53 (d,10) | 6.53 (d,10.0) |
| H-3 | 5.96 (s) | 5.97 (s) |
| H-7 | 5.37 (d,10) | 5.37 (d,10.0) |
| H-12 | 4.79 (d,7.4) | 4.79 (d,7.8) |
| H-10 | 3.97 (m,6.8,8.9) | 3.96 (dq,6.4,9.1) |
| H-11 | 2.03 (m,7.0,8.9,7.4) | 1.97 (ddq,6.8,9.1,7.8) |
| Me-10 | 1.47 (d,6.8) | 1.47 (d,6.4) |
| Me-11 | 1.17 (d,7.0) | 1.18 (d,6.8) |
| Me-6 | 0.97 (s), 0.91 (s) | 0.97 (s), 0.91 (s) |

| Assignment H# | Inophyllum C Literature | Inophyllum C Observed |
|---|---|---|
| Ph-4 | 7.3 | 7.3 (m) |
| H-8 | 6.56 (d,10) | 6.55 (d,10.0) |
| H-3 | 6.04 (s) | 6.05 (s) |
| H-7 | 5.42 (d,10) | 5.42 (d,10.0) |
| H-10 | 4.32 (m,6.6,11.5) | 4.32 (dq,6.3,11.1) |
| H-11 | 2.59 (m,7.2,11.5) | 2.57 (dq,6.9,11.1) |
| Me-10 | 1.56 (d,6.6) | 1.55 (d,6.3) |
| Me-11 | 1.24 (d,7.2) | 1.24 (d,6.9) |
| Me-6 | 0.98 (s), 0.95 (s) | 0.98 (s), 0.94 (s) |

| Assignment H# | Inophyllum D Literature | Inophyllum D Observed |
|---|---|---|
| Ph-4 | 7.3 | 7.3 (m) |
| H-8 | 6.59 (d,10.2) | 6.56 (d,10.0) |
| H-3 | 5.98 (s) | 5.98 (s) |
| H-7 | 5.36 (d,10.2) | 5.37 (d,10.0) |
| H-12 | 4.95 (d,2.0) | 4.94 (d,2.2) |
| H-10 | 4.59 (m,6.7,2.0) | 4.55 (dq,6.6,2.0) |
| H-11 | 1.99 (m,7.2,2.0,2.0) | 2.05 (ddq,7.3,2.0,2.2) |
| Me-10 | 1.45 (d,6.7) | 1.44 (d,6.6) |
| Me-11 | 0.83 (d,7.2) | 0.83 (d,7.3) |
| Me-6 | 0.95 (s) | 0.95 (s) |

| Assignment H# | Inophyllum E Literature | Inophyllum E Observed |
|---|---|---|
| Ph-4 | 7.3 | 7.3 (m) |
| H-8 | 6.56 (d,10) | 6.55 (d,10.0) |
| H-3 | 6.05 (s) | 6.05 (s) |
| H-7 | 5.42 (d,10) | 5.42 (d,10.0) |
| H-10 | 4.73 (m,6.8,3.7) | 4.73 (dq,6.6,3.4) |
| H-11 | 2.67 (m,7.2,3.7) | 2.71 (dq,7.2,3.4) |
| Me-10 | 1.44 (d,6.8) | 1.43 (d,6.6) |
| Me-11 | 1.18 (d,7.2) | 1.18 (d,7.2) |
| Me-6 | 0.97 (s) | 0.98 (s), 0.95 (s) |

| Assignment H# | Soulattrolide Literature | Inophyllum P Observed |
|---|---|---|
| Ph-4 | 7.3 | 7.3 (m) |
| H-8 | 6.53 (d,10) | 6.54 (d,10.0) |
| H-3 | 5.94 (s) | 5.97 (s) |
| H-7 | 5.35 (d,10) | 5.37 (d,10.0) |
| H-12 | 5.04 (d,3.2) | 5.04 (d,3.3) |
| H-10 | 4.31 (m,7.0,10.0) | 4.29 (dq,6.3,10.6) |
| H-11 | 1.78 (m,3.2,7.2,10.0) | 1.79 (ddq,3.3,7.0,10.6) |
| Me-10 | 1.44 (d,7.0) | 1.44 (d,6.3) |
| Me-11 | 1.16 (d,7.2) | 1.17 (d,7.0) |
| Me-6 | 0.93 (s) | 0.94 (s) |

STRUCTURE:

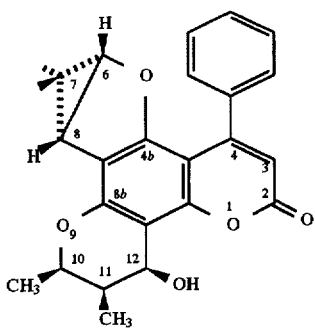

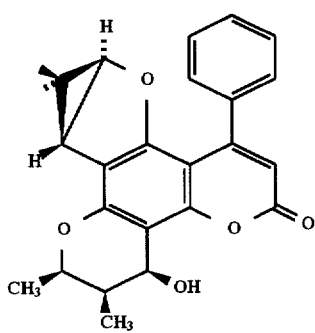

¹H NMR INFORMATION:

| Assignment H# | Inophyllum G1 Observed | Inophyllum G2 Observed |
|---|---|---|
| Ph-4 | 7.4 (m) | 7.4 (m) |
| H-3 | 6.01 (s) | 6.02 (s) |
| H-12 | 5.12 (dd,4.8,0.8) | 5.18 (dd,5.3,0.8) |
| H-10 | 4.46 (ddq,0.8,3.8,6.8) | 4.44 (ddq,0.8,3.3,6.8) |
| H-6 | 4.23 (d,5.7) | 4.21 (d,5.7) |
| H-8 | 2.46 (d,5.7) | 2.42 (d,5.7) |
| H-11 | 2.34 (ddq,3.8,4.8,7.1) | 2.33 (ddq,3.3,5.3,7.1) |
| Me-10 | 1.45 (d,6.8) | 1.45 (d,6.8) |
| Me-11 | 1.20 (d,7.1) | 1.18 (d,7.1) |
| Me-7 | 1.05 (s) | 1.05 (s) |

STRUCTURE:

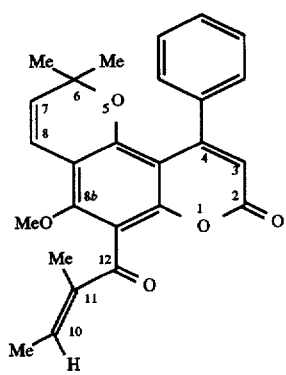

¹H NMR INFORMATION:

| Assignment H# | Calophyllolide Observed |
|---|---|
| Ph-4 | 7.34 (m) |
| H-10 | 6.58 (qq,1.3,6.9) |
| H-8 | 6.46(d,10.0) |
| H-3 | 6.02 (s) |
| H-7 | 5.48 (d,10.0) |
| OMe8b | 3.76 (s) |
| Me-11 | 2.01 (m) |
| Me-10 | 1.90 (dq,1.1,6.9) |
| Me-6 | 0.97 (s) |

5. Reverse Transcriptase Activity

RT inhibition was determined by a TCA precipitation assay as follows:

TCA-precipitation assay for HIV reverse transcriptase.

A heteropolymeric primer template was prepared by hybridizing a 691 nucleotide RNA molecule derived from the gag region of HIV [(+)-GAG$^{691}$, prepared as described in Mizrahi, V., Biochemistry, 28:9088–9094 (1989)], to a synthetic oligodeoxynucleotide (sequence: 5'-GGTCTACATAGTCTCTAAAA-3'). The primer template (10 nM) was incubated in reaction buffer (50 mM Tris-HCl, pH 7.8, 80 mM KCl, 6 mM MgCl$_2$, 10 mM DTT, 0.01 mg/ml BSA) with inhibitor, 10 μM dGTP, 10 μM dATP, and 28 μCi/ml of [3H]TYP (Amersham). Recombinant HIV reverse transcriptase (prepared as described in Mizrahi, et al., Arch. Biochem. Biophys., 273: 347–358, (1989)) was added to a concentration of 2–8 nM, and the reaction was incubated for 15 min at 37° C. (total reaction volume, 50 μL). The reaction was terminated with 50 μL of 20% TCA in 100 mM sodium pyrophosphate (ice cold) and chilled on ice for 15–30 min. The reaction mixture was filtered through glass fiber filters using a cell harvester, and the radioactivity that adhered to the filter was quantified using an LKB betaplate counter.

Scintillation proximity assay for HIV reverse tanscriptase.

HIV reverse transcriptase SPA enzyme assay system kits were obtained from Amersham (item number NK8972) and used as described in the package insert. Briefly, 10 μL of primer-template as supplied in the kit was added to 70 μL of dNTP/[3H]TTP solution. Ten μL of the inhibitor to be tested was added, followed by recombinant HIV RT (prepared as above) to a concentration of 2 nM. The reaction mixture was incubated for 10 min at room temperature and then terminated with 40 μL of 0.5M EDTA. Ten μL of streptavidin-SPA beads were added to each tube and the incorporated radioactivity was measured in an LKB betaplate counter. The results are presented below:

| Compound | IC$_{50}$(μM) |
|---|---|
| Inophyllum A | 9 |
| Inophyllum B | 0.3 |
| Inophyllum C | >50 |
| Inophyllum D | 30 |
| Inophyllum E | >50 |
| Inophyllum P | 0.6 |
| Calophyllolide | >50 |
| G1 | >50 |
| G2 | >50 |

Furthermore, Inophyllum B and Inophyllum P were shown to inhibit certain mutant forms of HIV RT that are resistant to TIBO. For example, HIV RT enzymes in which amino acid #181 was changed from tyrosine to either cysteine or isoleucine were inhibited by Inophyllums B and P with potency comparable to that observed with wild-type HIV RT.

6. HIV-1 Infectivity Inhibition Assay

Cytotoxicity was tested with the CD4+cell line, Molt4. The compounds of the present invention were dissolved in DMSO in order to maximize solubility and provide a common solvent system. The final concentration of DMSO in the cytotoxicity assay did not exceed 2% of the total volume. Cytotoxicity was measured as the inhibition of $^3$H-thymidine incorporation into the host cell's genome after exposure to the compounds of the present invention. Other cell lines that are available to one skilled in the art include CEM, AA5, MT-2 and H9 (see, Jacobs, *J. Nat'l Cancer Inst.*, 34:231 (1965)). As an alternative, cell viability could also be measured 18–20 hours after exposure to the compounds of the present invention by measuring the reductive capacity (e.g., MTT [3-(4,5-dimethylthiazol-2-yl)-2,5 diphenyl tetrazolium bromide] (see e.g., Pauwels et al., *J Virol Meth*, 20:309–321 (1988)) or XTT reagents), of cells in a microtiter format.

In addition, the compounds of the present invention were assayed via a virus neutralization, or HIV infectivity assay as follows:

Bulk Infection of Molt4 Cells.

Bulk infection is used to overcome variations inherent in individual well infections. Sufficient cells and diluted virus stock for an experiment are mixed together in a T-75 flask (Corning) so that the following ratio per well of virus and cells is maintained: 100 μl containing 45 TCID$_{50}$ of virus (IIIB Stock) mixed with 100 μl of Molt4 cells (3×10$^4$ cells/well or 3×10$^5$/ml). Virus is allowed to adsorb for 90 min. at 37° C. in CO$_2$ incubator. 200 μl/well of cell/virus mixture is then aliquoted into individual wells of a 24-well plate.

Inhibitor Dilutions

Appropriate 1/200 volumes of inhibitor dilutions at 200X final concentrations in 100% DMSO are added [i.e., to the 497.5 μl of virus infected cells, 2.5 μl of inhibitor dilution of 100% DMSO or 100% DMSO alone (for virus controls) is carefully added to appropriate wells]. Dilution series are generally 5-fold dilutions starting from 50 μg/ml.

Feeding Schedule

Cultures are fed with RPMI 1640+20% FBS containing 1× concentration of inhibitor series (i.e., starting concentrations present at beginning of experiment) at the following times and volumes:

Day 1—0.5 ml RPMI 1640+20% FBS+inhibitor

Day 4—0.5 ml RPMI 1640+20% FBS+inhibitor (Final volume in each well=1.5 ml)

Day 7—Harvest

Harvesting

Culture supernatants are harvested at 7 days post infection. Generally 90 μl of culture medium is transferred into a 96-well culture plate containing 10 μl 5% Triton X-100 in PBS. The plate is sealed, wiped with gauze saturated with 70% ethanol+detergent and stored at −80° C. until Micro RTs or p24 ELISAs are done. The results of HIV infectivity, inhibition is presented below:

| Cellular cytotoxicity (μM)[1] | IC$_{50}$ (μM)[2] | Selective Index[3] |
|---|---|---|
| Inophyllum A | 33 | NC[4] |
| Inophyllum B | 55 | 1.4 | 39 |
| Inophyllum C | 18 | | NC |
| Inophyllum D | 15 | | NC |
| Inophyllum E | 6.2 | | NC |
| Inophyllum P | 25 | 1.6 | 16 |
| Calophyllodide | 4.5 | | NC |
| TIBO | 19 | 0.19 | 100 |

[1]Measured via XTT
[2]50% Inhibitory concentration for cytopathicity by HIV
[3]Cytotoxycity/IC$_{50}$ ratio
[4]Not calculated 7. Calanolide Synthesis Calanolides A, C, D and related compounds were synthesized as follows.

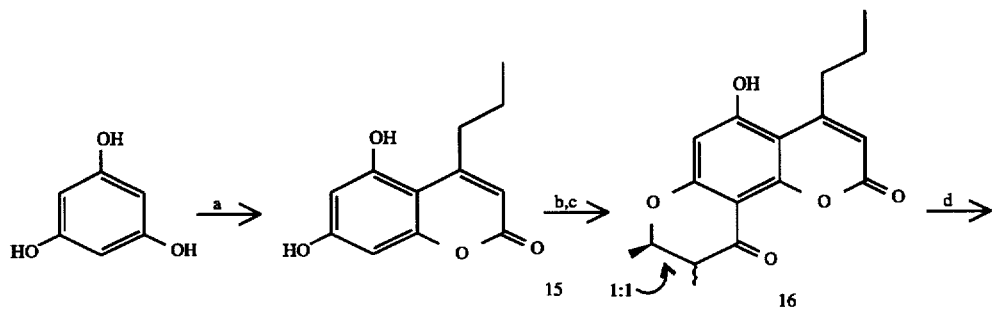

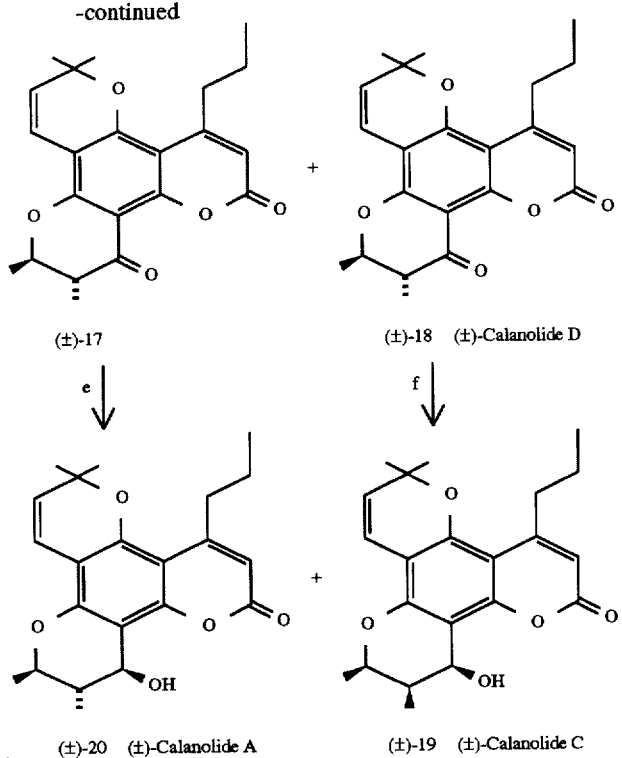

(±)-17      (±)-18   (±)-Calanolide D (±)-20   (±)-Calanolide A      (±)-19   (±)-Calanolide C $^a$(a) $C_3H_7COCH_2CO_2Et$, $CF_3SO_3H$ (neat), 0 ⟶ 25°C., 16 h (99%);

(b) tigloyl chloride, $AlCl_3$ (4 eq), $CS_2$, $PhNO_2$, 75°C., 14 h (87%);

(c) $K_2CO_3$, 2-butanone, 70°C., 2 h (89%);

(d) 1, 1-dimethylpropargylchloride (5 eq), $ZnCl_2$ (1.3 eq), $K_2CO_3$ (2.5 eq), (n-Bu)$_4$NI (1 eq), 2-butanone/DMF/$Et_2O$ (10:1:1), 70°C., 16 h ((±)-17: 34%; (±)-18: 27%);

(e) $NaBH_4$ (2 eq), $CeCl_3(H_2O)_6$ (1 eq), EtOH, 25°C. (59%);

(f) $NaBH_4$, EtOH, 25°C. (100%).

5,7-Dihydroxy-4-n-propylcoumarin (Compound 15).

A suspension of anhydrous phloroglucinol (20.0 g, 0.159 mol) in ethyl butrylacetate (26.3 g; 0.167 mol) was added over 30 min to 50 g of constantly stirred trifluoromethanesulfonic acid cooled in an ice bath. A drying tube was then fined to the reaction vessel and the mixture was stirred for 16h at 25° C., after which the resulting thick paste was combined with ice (200 g) and water (300 mL) with brisk stirring. After 30 min the solid material was collected by vacuum filtration and recrystallised from 95% ethanol to yield coumarin 15 (34.7 g; 99%) as lemon yellow crystals. mp 236°–238° C. $^1$H NMR (CDCl$_3$/CD$_3$OD 3:1): δ6.13(1H, d; J =2.3 Hz), 6.04(1H, d; J=2.3 Hz), 5.68(1H, s), 2.76(2H, t; J=7.4 Hz), 1.47(2H, tq; J =7.7, 7.4 Hz), 0.82(3H, t; J =7.7 Hz). $^{13}$C NMR (CDCl$_3$/CD$_3$OD 3:1): δ163.1, 160.7, 160.6, 157.3, 156.7, 107.8, 102.5, 99.2, 95.0, 37.7, 22.5, 13.4. Anal. calc. for $C_{12}H_{12}O_4 \cdot (H_2O)$: C, 60.50; H, 5.92. Found: C, 60.47; H, 5.92.

Compound 10

A solution of tigloyl chloride (3.0 g, 25 mmol) in carbon disulfide (2 mL) was added to a suspension of coumarin 15 (5.00 g, 22.7 mmol) and aluminium trichloride (12.9 g, 95.5 mmol) in carbon disulfide (50 mL) and the resulting mixture was stirred at 25° C. for 30 min. Nitrobenzene (20 mL) was then added and the mixture was heated to 75° C. for 14 h, then was poured into ice (50 g) and 1M HCl (200 mL). The mixture was extracted with 95:5 CHCl$_3$/MeOH (3×100 mL), the organic layer was dried over anhydrous $Na_2SO_4$ and the solvents were removed in vacuo to yield the crude product.

Flash chromatography (95:5 CH$_2$Cl$_2$/MeOH) furnished the desired product (5.97 g, 87 %) as a white solid. mp 266°–268° C. $^1$H NMR (CDCl$_3$/acetone-d$_6$~10:1): δ9.89 (1H, s); 9.50(1H, s); 6.44(1H, s); 6.41(1H, q; J=7.0 Hz), 5.87(1H, s), 2.95(2H, t; J=7.0 Hz); 1.72(3H, s) 1.67(3H, d; J=7.4 Hz); 1.21(2H, m); 1.01(3H, t; J=7.4 Hz). Anal. calc. for $C_{17}H_{18}O_5 \cdot (\frac{1}{8}H_2O)$: C, 67.04; H, 6.04. Found: C, 67.31; H, 6.00.

cis- and trans-2,3-Dimethylchromanones 16.

Potassium carbonate (4.12 g, 29.8 mmol) was added to a solution of compound 10 (3.00 g, 9.93 mmol) in 2-butanone (40 mL) and the mixture was heated to reflux for 2 h. The reaction mixture was cooled to room temperature, acidified with 1N HCl (150 mL) and extracted with ethyl acetate (2×200 mL). The combined organic layers were dried over anhydrous $Na_2SO_4$, and the solvents were removed in vacuo to yield a 1:1 mixture of isomeric chromanones 16 (2.66 g, 89 %) as a white solid. Anal. talc. for $C_{17}H_{18}O_5$: C, 67.54; H, 6.00. Found: C, 67.75; H, 6.05.

The pure trans and cis isomers of 16 were separated by HPLC (95:5 CH$_2$Cl$_2$/MeOH) for spectroscopic analysis. trans-2,3-Dimethylchromanone 16: $^1$H NMR (CDCl$_3$/CD$_3$OD 3:1): δ6.09(1H, s), 5.83(1H, s), 1.31(3H, d; J=6.3 Hz), 1.43(2H, tq; J=7.4, 7.3 Hz), 2.33(1H, dq; J =10.7, 5.7 Hz), 4.09(1H, dq; J=10.7, 6.3 Hz), 2.76(2H, t; J=7.4 Hz), 1.01(3H, d; J - 5.7 Hz), 0.82(3H, t; J=7.3 Hz). $^{13}$C NMR (CDCl$_3$/CD$_3$OD 3:1): δ190.6, 164.3, 161.9, 161.0, 159.3, 156.0, 109.9, 99.0, 104.1, 102.7, 78.9, 46.9, 38.0, 22.5, 19.1, 13.4, 10.2. MS (DCI/NH$_3$): m/z 320.3(M+NH$_4$)$^+$, 303.3(M+

H)⁺, 287.3.cis-2,3-Dimethyl-chromanone 16: ¹H NMR (CDCl₃/CD₃OD 3:1): δ6.11(1H, s), 5.85(1H, s), 4.48(1H, dq; J=6.6, 3.2 Hz), 2.77(2H, t; J=7.4 Hz), 2.44(1H, dq; J =7.2, 3.2 Hz), 1.47(2H, tq; J=7.4, 7.3 Hz), 1.22(3H, d; J=6.6 Hz), 0.96(3H, d; J=7.2 Hz), 0.82(3H, t; J=7.3 Hz). MS (DCI/NH₃): m/z 320.3(M+NH₄)⁺, 303.3(M+H)+, 287.3.

Chromenes (±)-17 and (±)-18.

Potassium carbonate (1.73 g, 12.5 mmol), propargyl chloride (2.55 g, 25.0 mmol) and tetra n-butyl ammonium iodide (1.85 g, 5.00 mmol) were added to a suspension of compound 16 (1.51 g, 5.00 mmol; 1:1 mixture of cis- and trans-dimethyl isomers) in 2-butanone (65 mL) and dry DMF (6.5 mL). The reaction mixture was heated to 60° C. for 1 h, then anhydrous ZnCl₂ (6.50 mmol, 6.65 mL of a 1M solution in ether) was added. The mixture was heated to 70° for 16 h, then cooled and quenched with saturated aqueous NH₄Cl (125 mL), extracted with ethyl acetate (2×100 mL), washed with brine and dried over Na₂SO₄. The solvents were removed in vacuo to give an oil (2.28 g) which was purified by flash chromatography (2:3 EtOAc/hexanes) to provide chromenes (±)-17 (622 mg, 34%) and (±)-18 (486 mg, 27%) as white solids. For compound (±)-17: mp 130°-132° C. ¹H NMR (CDCl₃/CD₃OD 3:1): δ6.67(1H, d; J=11.8 Hz), 6.09(1H, s), 5.58(1H, d; J=11.8 Hz), 4.26(1H, dq; J=10.7, 6.3 Hz), 1.63(2H, tq; J=7.4, 7.3 Hz), 1.52(2×3H, s), 2.33(1H, dq; J=10.7, 5.7 Hz), 2.82(2H, t; J=7.4 Hz), 1.46(3H, d; J=6.3 Hz), 1.18 (3H, d; J=5.7 Hz), 0.92(3H, t; J=7.3 Hz). MS (DCI/NH₃): m/z 386.1(M+NH₄)⁺, 369.0(M+H)⁺, 186.1, 168.1, 151.0. Anal. calc. for C₂₂H₂₄O₅: C, 71.72; H, 6.57. Found: C, 71.57; H, 6.64. For compound (±)-18: mp 130°-131° C. ¹H NMR (CDCl₃/CD₃OD 3:1): δ6.78(1H, d; J=11 Hz), 5.98(1H s), 5.61(1H, d; J =11 Hz), 4.69(1H, dq; J=6.6, 3.2 Hz), 2.85(2H, t; J=7.4 Hz), 2.61(1H, dq; J=7.2, 3.2 Hz), 1.63(2H, tq; J=7.4, 7.3 Hz), 1.50(2×3H, s), 1.42(3H, d; J=7.0 Hz), 1.14(3H, d; J =7.2 Hz), 1.01(3H, t; J =7.3 Hz). MS (DCI/NH₃): m/z 386.2(M+NH₄)⁺, 369.1 (M+H)⁺, 186.1, 168.1, 151.1. Anal. Calc. for C₂₂H₂₄O₅: C, 71.72; H, 6.57. Found: C, 71.70; H, 6.70.

The ¹H NMR and mass spectral data for compound (±)-18 were identical with those reported for calanolide D. Sodium borohydride reduction of (±)-18 proceeded quantitatively to (±)-19 (mp 54°-56° C.), whose spectral data matched those of calanolide C. Sodium borohydride reduction of ketone (±)-17 was less selective, affording a 7:3 mixture of (±)-calanolide A ((±)-20) and its hydroxy epimer (90% yield), which were not easily separable. However, Luche reduction (Gemal et at., J. Am. Chem. Soc., 103:5454 (1981)) of ketone (±)-17 was highly stereoselective, providing (±)-20 (mp 56°-58° C.) in 59% yield after chromatography. The ¹H NMR spectrum, mass spectrum, and HIV-1 RT-inhibitory potency of (±)-20 were in full agreement with the data reported for natural calanolide A. This five-step synthesis of (±)-calanolide A (ca. 15% overall yield) forms a practical basis for chemical studies of the calanolide class of potential (AIDS) therapeutics.

(±)-Calanolide A ((±)-20).

Sodium borohydride (30 mg, 0.81 mmol) was added in one portion to a stirring mixture of chromene (±)-17 (150 mg, 0.41 mmol) and CeCl₃(H₂O)₇ (155 mg, 0.42 mmol) in ethanol .(5 mL) at 25° C. After 30 min the mixture was diluted with water and extracted with ethyl acetate. The organic layer was dried (Na₂SO₄) and concentrated, and the residue was purified by flash chromatography (1:6 EtOAc/hexanes) to provide pure (±)-20 (88 mg, 59% yield). mp 56°-58° C. ¹H NMR (CDCl₃): δ6.63(1H, d; J =10 Hz), 5.95(1H, s), 5.55(1H, d; J=10 Hz), 4.73(1H, d; J=7.9 Hz), 3.95(1H, m), 3.55(1H, bs), 2.87(2H, m), 1.93(1H, m), 1.67 (2H, m), 1.51(3H, s), 1.46(3H, s), 1.47(3H, d; J=6.3 Hz), 1.15(3H, d; J=6.8 Hz), 1.04(3H, t; J=7 Hz). MS (ESI): m/z 371.2 (M+H)⁺, 353.2. Anal. Calc. for C₂₂H₂₆O₅.(¼H₂O): C, 70.47; H, 7.12. Found: C, 70.60; H, 7.17.

Reduction of Chromene (±)-17 with NaBH₄:

Sodium borohydride (25 mg, 0.74 mmol) was added to a stirring suspension of chromene (±)-17 (100 mg, 0.27 mmol) in ethanol (5 mL) at 25 ° C. After 30 min, extractive workup and flash chromatography (1:8 EtOAc/hexanes) provided a 7:3 mixture (by ¹H NMR) of (±)-20 and its hydroxy epimer (90 mg, 90% yield).

(±)-Calanolide C ((±)-19):

Reduction of chromene (±)-18 (97 mg, 0.26 mmol) with sodium borohydride (30 mg, 0.88 mmol) in ethanol (5 mL) as described immediately above, followed by extractive workup, provided pure compound (±)-19 (97 mg, 100% yield) as a single isomer. mp 54°-56° C. ¹H NMR (CDCl₃): δ6.63(1H, d; J=10 Hz), 5.94(1H, s), 5.54(1H, d; J =10 Hz), 5.09(1H, t; J=6, 1 Hz), 4.39(1H, dq; J=6.7, 3.3 Hz), 3.29(1H, d; J=1 Hz; OH), 2.92(1H, m), 2.86(1H, m), 2.28(1H, m), 1.66(2H, m), 1.49(6H, s), 1.42(3H, d; J=7 Hz), 1.14(3H, d; J=7 Hz), 1.04(3H, t; J=7 Hz). MS (ESI): m/z 371.2 (M+H)⁺, 353.0. Anal. Calc. for C₂₂H₂₆O₅.(¼H₂O): C, 70.47; H, 7.12. Found: C, 70.50; H, 7.17.

The following ketone was synthesized using the procedures described in step "d" of the synthesis except that methylacryloyl chloride was used in place of 1,1-dimethyl propargyl chloride.

1HNMR(CDCl₃, 400MHz) a 6.65(d, 1H, J=10Hz), 6.05(s, 1H), 5.6(d, 1H, J=10Hz), 4.62(m, 1H), 2.91(dd,2H, J=9Hz), 2.61(m,2H), 1.62(m,2H), 1.55(s,3HO, 1.54(d, 3H, J=7Hz), 1.52(s, 3H), 1.029 (t, 3H, J=7Hz).

The following alcohols were synthesized by NaBH₄ reduction of the ketone as described above, then separated via HPLC.

6.63(d, 1H, J=10Hz), 5.95(s, 1H), 5.54(d, 1H, J=10Hz), 5.173(bs, 1H), 4.44(m, 1H), 3.1(s, 1H), 2.9(m, 2H), 1.6–2.1 (m,4H), 1.498 (s, 3H), 1.49 (d, 3H, J=7Hz), 1.474(s, 3H), 1.03(t, 3H, J=7Hz).

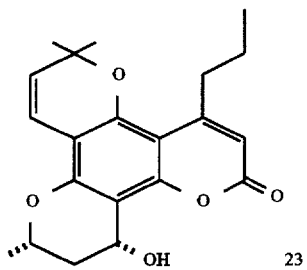

23

6.63(δ, 1H, J=10Hz), 5.95(s, 1H), 5.52(d, 1H, J=10Hz), 5.20(t, 1H, J=7Hz), 4.35(m, 1H), 3.6(bs, 1H), 2.90(m, 2H), 2.35(m, 1H), 1.95(m, 1H), 1.5–1.7(m, 2H), 1.50(s, 3H), 1.49(d, 3H, J=7Hz), 1.47(s, 3H), 1.03(t, 3H, J=7Hz).

| Reverse Transcriptase Activity: | |
| --- | --- |
| Compound 22 | Compound 23 |
| $IC_{50}(\mu M) = 1.78$ | $IC_{50}(\mu M) = 0.6$ |

The above examples and description fully disclose the present invention, including preferred embodiments thereof. This invention, however, is not limited to the precise embodiments described herein, hut encompasses all modifications within the scope of the art of the following claims.

What is claimed is:

1. A process for preparing a compound of the structure:

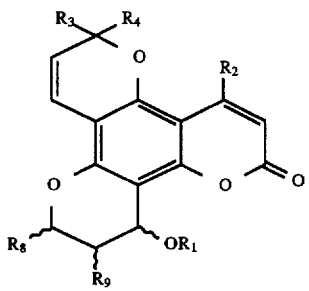

wherein $R_1$ is H, acyl, $COCHR_5NR_6R_7$, $P(O)(OH)_2$ or $S(O)(OH)_2$; wherein:

$R_5$ is H or a side chain of any naturally occurring amino acid; and $R_6$ and $R_7$ are independently selected from the group consisting of H and $C_{1-6}$ alkyl; and $R_6$ and $R_7$ can be taken together to form a 5–7 membered saturated heterocyclic ring containing said nitrogen;

$R_2$ is H, hydroxyl, $C_{1-6}$ alkyl, $C_{1-6}$ alkylamino, di($C_{1-6}$ alkyl)amino, 1-amino-$C_{1-8}$ alkyl, $C_{1-8}$ alkyl-amino-$C_{1-8}$ alkyl, di-($C_{1-6}$ alkyl)amino $C_{1-8}$ alkyl, cyclohexyl, aryl or hetemcycle, wherein aryl or heterocycle may each be unsubstltuted or substituted with one or more of the following: $C_{1-6}$ alkyl, $C_{1-6}$ alkoxy, hydroxy-$C_{1-4}$ alkyl, amino, $C_{1-6}$ alkylamino, di($C_{1-6}$ alkyl)amino, 1-amino-$C_{1-8}$ alkyl, $C_{1-8}$ alkyl-amino-$C_{1-8}$ alkyl, di-($C_{1-6}$ alkyl)amino $C_{1-8}$ alkyl, hydroxyl, nitro, azido or halogen; and $R_3$, $R_4$, $R_8$ and $R_9$ are independently selected from the group consisting of H, methyl and ethyl;

or a pharmaceutically acceptable salt thereof;

which comprises:

(a) reaction of phloroglucinol with a β-ketoester under acid catalysis;

(b) acylation with a substituted acryloyl halide and subsequent base-catalyzed ring closure;

(c) chromene ring formation, by reacting with a propargyl halide in the presence of base, acid and nBu4NI (or KI) and heating the mixture; and (d) reduction of the keto group in ring position 12; with the proviso that when $R_2$ is H, then the ester reacting with phloroglucinol is propiolate ester.

2. The process of claim 1 wherein the acid catalyst is trifluoromethanesulfonic acid.

3. The process of claim 1, wherein the acid is selected from the group consisting of: $ZnCl_2$, $BCl_3$, $Et2AlCl$, $TiCl_4$, $AlCl_3$, $AgNO_3$ and mercury salts.

4. The process of claim 3 wherein the acid is $ZnCl_2$.

5. The process of claim 1 wherein the chromene ring formation occurs at 50° C. to 120° C.

6. The process of claim 5 wherein the chromene ring formation occurs at 70° C.

7. The process of claim 1 wherein the reduction is catalyzed by sodium borohydride ($NaBH_4$).

8. The process of claim 1 wherein the reduction is catalyzed by sodium borohydride ($NaBH_4$) and cerium trichloride ($CeCl_3$).

* * * * *